Oct. 2, 1951 M. L. WHISLER Plant Pat. 1,042
ROSE PLANT
Filed June 22, 1950
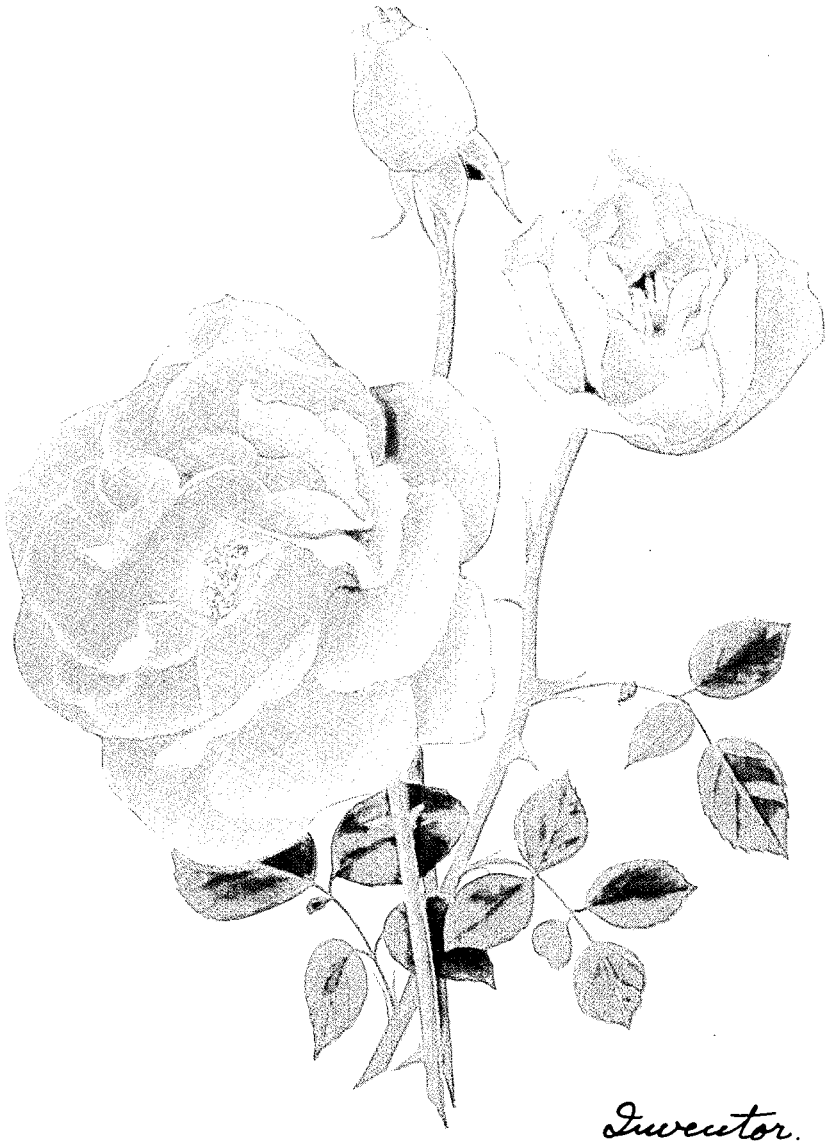
Inventor.
M. L. Whisler
By: Robb & Robb
Attorneys.

Patented Oct. 2, 1951

Plant Pat. 1,042

UNITED STATES PATENT OFFICE 1,042

ROSE PLANT

Milton L. Whisler, Van Nuys, Calif., assignor to Germain's, Inc., Van Nuys, Calif., a corporation of California Application June 22, 1950, Serial No. 169,634

1 Claim. (Cl. 47—61)

The present invention relates to a new and distinct variety of rose plant of the hybrid polyantha class, originating as a cross of the varieties "World's Fair" (Plant Patent No. 362) × "Adolf Grille" (Plant Patent No. 475).

As a result of this cross, I have produced a rose which is distinguished from its parents as well as from other varieties, but which more nearly resembles the variety "Donald Prior" (Plant Patent No. 377) than any other. This latter variety is a hybrid polyantha rose which is characterized by its vigorous bush, striking masses of Spectrum Red to Carmine color, continuity of bloom, and luxuriant green foliage.

The new variety differs importantly from "Donald Prior," however, by virtue of the brighter color of its flowers, longer stems, and more leathery foliage. In addition, the new variety is characterized by its freedom of bloom, its bushy and much branched habits of growth, its unusually long stems for a rose of this class, and by the ability of holding the color of its flowers at all times.

Asexual reproduction of this new variety by cuttings, budding and grafting at Van Nuys, California, shows that the foregoing characteristics come true to form and are established and transmitted through succeeding propagations.

The accompanying drawing shows specimens of the new variety, with the flowers and foliage in different stages of development.

The following is a detailed description of the new variety, with color terminology in accordance with Horticultural Color Chart of the British Color Council, except where ordinary dictionary significance is obvious:

Type: Half-hardy; bush; outdoor; seedling; for garden decoration.
Class: Hybrid polyantha.
Breeding: Seedling.
*Seed parent.*—"World's Fair."
*Pollen parent.*—"Adolf Grille."
Propagation: Holds its distinguishing characteristics through succeeding propagations by cuttings, budding and grafting.

*Flower*

Locality where grown: Van Nuys, California.
Flowers borne: Several to stem; in irregular cluster; on normal, medium length stems.
Quantity of bloom: Free; outdoors.
Continuity: Continuous.
Fragrance: Moderate; spicy.
Bud:
*Peduncle.*—Long; medium heavy; erect; light bronze; almost smooth; few brown prickles.
*Before calyx breaks.*—Size—medium. Form—short; pointed; without foliaceous appendages on the surface of the bud; with slender, much cut foliaceous parts extending beyond the tip of the bud equal to three-fourths of its length. Color—Chrysanthemum Crimson, Plate 824.
*As calyx breaks.*—Color—Cardinal Red, Plate 822.
*As first petal opens.*—Size—medium. Form—short; pointed. Color—outside: Cardinal Red, Plate 822/1; inside: Cardinal Red, Plate 822/1.
*Opening.*—Bud opens up well.

Bloom:
*Size, when fully open.*—Medium; 3 to 3½ inches.
*Petalage.*—Semi-double; from 15 to 18 petals arranged irregularly.
*Form.*—Cupped at first; becoming open; petals being at first rolled outward; becoming later, at maturity, flat cupped.

Petals: Thick; soft; with inside velvety and outside satiny.
*Shape.*—Outside and intermediate—obovate.

This description of a newly opened flower was made from a rose grown outdoors in the month of August, 1949, at Van Nuys, California:

*Color.*—*Outside petal*—outside surface: Currant Red, Plate 821; inside surface: Currant Red, Plate 821/3. *Intermediate petal*—outside surface: Currant Red, Plate 821; inside surface: Currant Red, Plate 821/3. *Inner petal*—outside surface: Currant Red, Plate 821; inside surface: Currant Red, Plate 821/3.

This description was made from a rose that was open for three days outdoors in the month of August, 1949, at Van Nuys, California:

*Color.* — *Outside petal* — outside surface: Chrysanthemum Crimson, Plate 824/3; inside surface: Cardinal Red, Plate 822/1. *Inside petal*—outside surface: Chrysanthemum Crimson, Plate 824/3; inside surface: Cardinal Red, Plate 822/1.
*General color effect.*—Newly opened flower—Currant Red, Plate 821. Three days open—Cardinal Red, Plate 822/1.
*Behavior.*—Drop off cleanly.
*Flower longevity.*—On bush in garden—4 days in August. Cut roses grown outdoors kept at living room temperatures—4 days in August.

*Reproductive Organs*

Stamens: Medium number.
Filaments: Long; reddish; most with anthers.
Anthers: Medium size; yellow; all open at once. Color—Reddish with yellow margin.

Pollen: Abundant; yellow.
Pistils: Few.
Styles: Uneven; long; medium heavy; loosely bunched.
Stigma: Yellow.
Ovaries: All enclosed in calyx.
Hips: Ovoid; green grey; moderately smooth; walls thick and dry.
Sepals: Falling soon; moderately long; recurved.

*Plant*

Foliage:

*Leaves.*—Compound of five leaflets; normal abundance; medium size; heavy; leathery.

*Leaflet.* — Shape — oval with apex acute; base—round; margin—simply serrate.

*Color.* — Mature — upper surface: normal green; under surface: light green. *Young* —upper surface: light green bronze; under surface: very green.

*Rachis.*—Medium heavy. Upper side—grooved, hairy; under side—sparsely prickly.

*Stipules.*—Medium length; wide; with medium length points turning out at an angle of 45°.

*Disease.*—Resistant to mildew.

Growth:

*Habit.*—Bushy; much branched.

*Growth.*—Free.

*Canes.*—Medium heavy.

*Main stems.*—Color—dull green. *Thorns*—few; medium length; straight; with long, narrow base. *Prickles and hairs*—none.

*Branches.*—Color—dull green. *Thorns*—several; medium length; straight; with long, narrow base. *Prickles* — few; brown. *Hairs*—none.

*New shoots.*—Color—bright bronze. *Thorns* —several; medium length; straight; with narrow base. *Prickles*—several; reddish. *Hairs*—none.

I claim:

A new and distinct variety of rose plant of the hybrid polyantha class, characterized as to novelty by its freedom of bloom, its bushy and much branched habits of growth, its unusually long stems for a rose of this class, its leathery foliage, the bright color of its flowers, and by the ability of its flowers to hold their color at all times, substantially as shown and described.

MILTON L. WHISLER.

No references cited.